(12) United States Patent
Hauger et al.

(10) Patent No.: US 8,922,882 B2
(45) Date of Patent: Dec. 30, 2014

(54) IMAGING SYSTEM

(75) Inventors: Christoph Hauger, Aalen (DE);
Markus Seesselberg, Aalen (DE);
Martin Hacker, Jena (DE); Keith O'Hara, San Ramon, CA (US)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 13/116,358

(22) Filed: May 26, 2011

(65) Prior Publication Data
US 2011/0228218 A1 Sep. 22, 2011

Related U.S. Application Data

(63) Continuation of application No. PCT/EP2009/008433, filed on Nov. 26, 2009.

(60) Provisional application No. 61/118,213, filed on Nov. 26, 2008.

(51) Int. Cl.
| | | |
|---|---|---|
| G02B 23/12 | (2006.01) |
| G02B 21/06 | (2006.01) |
| G01B 9/02 | (2006.01) |
| G01J 3/45 | (2006.01) |
| A61B 3/10 | (2006.01) |
| A61B 3/13 | (2006.01) |

(52) U.S. Cl.
CPC .......... *G01B 9/0203* (2013.01); *G01B 9/02004* (2013.01); *G01B 9/02035* (2013.01); *A61B 3/102* (2013.01); *G01B 9/02091* (2013.01); *A61B 3/13* (2013.01); *G01B 9/02044* (2013.01)
USPC ............................ 359/353; 359/388; 356/456

(58) Field of Classification Search
USPC ................. 351/200, 205, 206, 222, 221, 211; 359/237, 290–292, 298, 353, 355, 383, 359/388, 377, 385; 356/456, 479, 484, 497; 250/227.19, 227.2, 227.27, 227.22
See application file for complete search history.

(56) References Cited

U.S. PATENT DOCUMENTS

| | | | |
|---|---|---|---|
| 5,493,109 A | | 2/1996 | Wei et al. |
| 5,975,697 A | | 11/1999 | Podoleanu et al. |
| 6,004,314 A | * | 12/1999 | Wei et al. .................... 606/12 |

(Continued)

FOREIGN PATENT DOCUMENTS

| | | |
|---|---|---|
| DE | 299 05 969 U1 | 8/1999 |
| DE | 10 2005 046 690 A1 | 5/2006 |

(Continued)

OTHER PUBLICATIONS

G.J. Tearney et al., "High-speed phase- and group-delay scanning with a grating-based phase control delay line", *Optics Letters*, vol. 22, No. 23, pp. 1811-1813, 1997.

(Continued)

*Primary Examiner* — Thomas K Pham
*Assistant Examiner* — Brandi Thomas
(74) *Attorney, Agent, or Firm* — Patent Portfolio Builders PLLC (57) ABSTRACT

Imaging systems are provided allowing examination of different object regions spaced apart in a depth direction by visual microscopy and by optical coherence tomography. An axial field of view and a lateral resolution is varied depending on which object region is examined by the imaging system. The proposed imaging systems are in particular applicable for thorough examination of the human eye.

51 Claims, 5 Drawing Sheets

(56) References Cited

U.S. PATENT DOCUMENTS

| | | | |
|---|---|---|---|
| 6,212,006 B1 | 4/2001 | Reiner | |
| 7,440,112 B2* | 10/2008 | Kurokawa et al. | 356/495 |
| 7,852,492 B2* | 12/2010 | Berner | 356/605 |
| 2005/0089239 A1* | 4/2005 | Brajovic | 382/266 |
| 2006/0066869 A1 | 3/2006 | Ueno et al. | |
| 2007/0024856 A1 | 2/2007 | Izatt et al. | |
| 2007/0076220 A1 | 4/2007 | Kawahara | |
| 2007/0263226 A1* | 11/2007 | Kurtz et al. | 356/492 |
| 2008/0117432 A1 | 5/2008 | Reimer et al. | |
| 2008/0117503 A1 | 5/2008 | Reimer et al. | |
| 2008/0117504 A1* | 5/2008 | Reimer et al. | 359/389 |
| 2008/0192236 A1 | 8/2008 | Smith et al. | |

FOREIGN PATENT DOCUMENTS

| | | |
|---|---|---|
| DE | 10 2007 019 677 A1 | 5/2008 |
| DE | 10 2007 019 678 A1 | 5/2008 |
| DE | 10 2007 019 679 A1 | 5/2008 |
| DE | 10 2007 019 680 A1 | 8/2008 |
| JP | 2006-95318 A | 4/2006 |
| JP | 2007-508558 A | 4/2007 |
| JP | 2007-121262 A | 5/2007 |
| JP | 2007-212376 A | 8/2007 |
| JP | 2008-520992 A | 6/2008 |
| JP | 2008-529669 A | 8/2008 |
| WO | WO 98/38907 A1 | 9/1998 |
| WO | 2006/054116 A2 | 5/2006 |

OTHER PUBLICATIONS

International Search Report and Written Opinion of the International Searching Authority mailed on Jun. 9, 2010 in corresponding International Application No. PCT/EP2009/008433, 18 pages.

Japanese Office Action issued in corresponding Japanese Patent Application No. 2011-537886, mailed Sep. 24, 2013.

* cited by examiner

Fig. 4

IMAGING SYSTEM

CROSS-REFERENCES TO RELATED APPLICATIONS

This application claims priority to and is a continuation of International Patent Application No. PCT/EP2009/008433, filed Nov. 26, 2009, which claims the benefit of U.S. Provisional Patent Application No. 61/118,213, filed Nov. 26, 2008. The disclosures of PCT/EP2009/008433 and 61/118,213 are hereby incorporated by reference in their entirety for all purposes

FIELD OF THE INVENTION

The present invention relates to optical coherence tomography (OCT) systems and to imaging systems including an OCT system. The invention in particular relates to imaging systems including an OCT system and a microscope system.

BACKGROUND OF THE INVENTION

Optical coherence tomography (OCT) is an optical interferometric method for gaining structure information of an object. The object is disposed in a measurement arm of an interferometer and illuminated with a measuring light, measuring light returned from the object is superimposed with a reference light having traversed a reference arm of the interferometer such that the superimposed portions of light may interfere with each other. Intensities of the interfering light are detected. Measuring light returning from different portions of the object experiences different phase differences relative to the reference light, resulting in different detected light intensities after superposition with the reference light. It is possible to obtain information relating to structures of the object by analyzing interference patterns obtained by such measurements.

OCT is particularly suitable to obtain high resolution information of tissue volumes of the human eye.

Different types of OCT apparatuses have been developed for imaging of the anterior portions of the eye and of the posterior portions of the eye.

Surgical microscopes are used to provide images of an eye to a surgeon. The images are obtained by optically imaging extended portions of the eye via oculars such that the surgeon may look into the oculars to perceive the images, or the extended portions of the eye are optically imaged onto a camera having an array of pixels, and light intensities detected by the pixels are displayed on a display, such as a monitor or a head mounted display carried by the surgeon. Optical interference is not involved in such imaging. Surgical microscopes are often embodied as stereoscopic microscopes providing different views of the object to the left and right eyes of the surgeon such that the object is perceived as having a three dimensional structure.

It has been found desirable to provide OCT systems having an extended applicability and to provide imaging systems including a microscopy system and an OCT system.

SUMMARY OF THE INVENTION

The present invention was made in view of the aforementioned problems.

According to some embodiments, the invention provides imaging systems combining a microscope system and an OCT system.

According to some other embodiments, the invention provides imaging systems for imaging the anterior portion of the eye.

According to still some other embodiments, the invention provides imaging systems for imaging the posterior portion of the eye.

According to still some other embodiments, the invention provides imaging systems for imaging both the anterior and posterior portions of the eye.

According to still some further embodiments, the invention provides imaging systems combining a microscopy system and an OCT system for imaging both the anterior and posterior portions of the eye.

According to an exemplary embodiment, an imaging system comprises an objective lens system; a light source for generating a beam of OCT measuring light; and an illumination optics having adjustable optical power, wherein the imaging system provides a microscope facility for imaging an object region to an image region using the objective lens system, and an OCT facility, wherein the light source, the objective lens system and the illumination optics are configured such that the beam of OCT measuring light traverses the illumination optics and the objective lens system for illuminating at least part of the object region with the OCT measuring light having an adjustable lateral width.

According to another exemplary embodiment, an imaging system provides an OCT facility including a light source for generating a beam of OCT measuring light and an illumination optics having variable optical power for adjusting a lateral width of the beam of OCT measuring light illuminating at least part of an object region; and a detection system comprising a detector for detecting plural spectral portions of OCT measuring light returned from the object region and superimposed with reference light, wherein at least one of the following holds: a spectral width of the OCT measuring light illuminating the object region is adjustable; a spectral width of the detected plural spectral portions is adjustable.

The lateral width of a waist of the beam of the OCT measuring light illuminating the object region is adjustable. Thus, a lateral extension, i.e. an extension transverse, in particular orthogonal, to a direction of the OCT measuring light impinging onto the object region can be controlled by the imaging system. In particular, the OCT measuring light illuminating at least part of the object region forms a spot at the object region whose size is controllable. In particular the size of the spot of the OCT measuring light illuminating the object region may be changed in a range from 100 nm to 100 μm. Further, the spot illuminating at least part of the object region may be scanned across the object region to enable acquiring an image of the object region. The spot may have a substantially circular shape or an elongated shape, such as an ellipsoidal shape.

Changing the lateral width of the OCT measuring light may also comprise defocusing the OCT measuring light at the object region. Such defocusing may be performed in dependence of a visual defect of an examined human eye.

In particular, the OCT measuring light is light having a low coherence length to perform white light interferometry.

Depending on the material comprised in the investigated object, a mean wavelength of the spectrum of the OCT measuring light and other physical properties, the intensity of the OCT measuring light penetrating the object exponentially decreases characterized by a particular penetration depth. The penetration depth may amount for example to 1 mm to 3 mm for biological objects such as tissue, if the mean wavelength of the OCT measuring light is in a range of for example 800 nm to 1300 nm. OCT measuring light penetrated into the object up to a particular depth within the object, interacts with material present within a volume at that depth which comprises scattering and reflection processes. In particular, a reflectivity within a volume of the object depends on a refractive index and/or a gradient of the refractive index of the material within the particular volume inside the object. In particular, an intensity of OCT measuring light emanating at a particular depth within the object depends on a reflectivity at this depth within the object.

The OCT measuring light having interacted with the object and emanating from the object, thereby having traversed a particular probing optical beam path length, is superimposed with reference light having traversed a particular reference optical beam path length, and is detected. An intensity of the detected superimposed light depends on a coherence length of the OCT measuring light and a difference between the probing optical beam path length and the reference optical beam path length. Only if this difference between the probing optical beam path length and the reference optical beam path length is less than the coherence length of the OCT measuring light an interference signal can be detected.

Different variants of OCT differ in the way the object is probed at different depths and also in the way the superimposed light is detected.

In Time-Domain OCT (TD-OCT) probing different depths of the object (i.e. performing an axial scan) is performed by varying the reference optical beam path length, for example by displacing a reflecting surface from which the reference light is reflected. A disadvantage of this variant of OCT is however, that a mechanical displacement of the reflecting surface must be performed involving uncertainties and inaccuracies of the amount of displacement as well as inaccuracies of maintaining a proper orientation of the reflecting surface.

Frequency-Domain OCT (FD-OCT) is another variant of OCT. Herein, the reference light is also reflected at a reflecting surface, but this reflecting surface does not need to be displaced in order to probe different depths of the object. Instead, structure information about the object in different depths, i.e. in particular reflectivities in different depths, are obtained by detecting intensities of the superimposed light in dependence of a wavelength of the superimposed light.

Embodiments of the present invention employ in particular principles of Frequency-Domain OCT. In particular, embodiments of the present invention employ principles of two subtypes of Frequency-Domain OCT, i.e. Spectral-Domain OCT (SD-OCT), incidentally also called Fourier-Domain OCT, and Swept-Source OCT (SS-OCT).

In Spectral-Domain OCT the light superimposed of reference light and OCT measuring light returned from the object is spectrally dispersed using a spectrometer, to spatially separate plural spectral portions of the superimposed light. Intensities of these spatially separated plural spectral portions of the superimposed light are then detected by a positionally resolving detector. Thereby, the positionally resolving detector may comprise plural detector segments each of which receives a spectral portion of the superimposed light. The positionally resolving detector then supplies electrical signals corresponding to the intensities of the plural spectral portions representing a spectrum of the superimposed light. By Fourier transformation of the spectrum of the superimposed light a distribution of reflectivities of the object along the depth direction, i.e. an axial direction, is obtained.

The OCT measuring light illuminating at least part of the object region may be characterized by its spectrum, i.e. its normalized intensities in dependence of a wavelength. The spectrum of the OCT measuring light in turn may be characterized by a peak wavelength of the OCT measuring light and a spectral width of the OCT measuring light. The spectral width of the OCT measuring light characterizes a width of a wavelength range within which most of the intensity of the OCT measuring light is comprised. In particular, the spectral width may be determined to be a minimum of a difference between an upper wavelength and a lower wavelength, wherein an intensity of the OCT measuring light having wavelengths between the lower wavelength and the upper wavelength amounts to 90% of a total intensity of the OCT measuring light. The peak wavelength of the OCT measuring light may be defined to be a mean of the lower wavelength and the upper wavelength, it may be defined as a mean wavelength of the spectrum of the OCT measuring light, or it may be defined as a wavelength for which the spectrum of the OCT measuring light has a maximum.

When principles of Spectral-Domain OCT are employed in embodiments according to the present invention the light source generates a beam of OCT measuring light having a peak wavelength between 800 nm and 1300 nm and having a spectral width between 5 nm and 100 nm, in particular between 15 nm and 30 nm. A coherence length of the OCT measuring light is inversely proportional to the spectral width of the OCT measuring light. In the case, where principles of Spectral-Domain OCT are employed, the spectral width of the OCT measuring light does not need to be adjustable. In this case the spectral width of the OCT measuring light illuminating the object region is related to a limit of an achievable axial resolution. Further, in this case, the spectral width of the detected plural spectral portions of the superimposed light may be adjustable. The detection system may in this case comprise a positionally resolving detector having plural detector segments. Each segment of the detector may detect an intensity of a particular spectral portion of the superimposed light. For dispersing the superimposed light in the plural spectral portions a dispersion system, for example a diffraction grating or the like, is provided.

Another subtype of Frequency-Domain OCT is Swept-Source OCT (SS-OCT). According to embodiments of the present invention principles of SS-OCT are employed. Hereby, the object region is illuminated with OCT measuring light having a narrow spectral width corresponding to a relatively long coherence length compared with the largest desired axial field-of-views. During a measurement the peak wavelength of the OCT measuring light may be swept over a range of wavelengths spanning preferably at least 10 nm and up to 200 nm and more. Therein the peak wavelength being in a range between 800 nm and 1300 nm, is varied in dependence of time, i.e. the peak wavelength is swept while detecting OCT measuring light returned from the object and superimposed with reference light by a detector, such as a photodiode. Detecting the superimposed light upon sweeping the peak wavelength of the OCT measuring light enables acquiring a spectrum of the superposed light. Again, as in the case of Spectral-Domain OCT, structure information about the object may be obtained by Fourier transformation of the acquired spectrum of the superimposed light. Thus, when principles of Swept-Source OCT are employed in embodiments of the present invention, the detection system does not need to comprise a dispersion apparatus for spectrally dispersing the superimposed light. However, in this case the spectral width of the OCT measuring light illuminating the object region may be adjustable. This can be achieved for example by arranging at least one spectral filter in a beam path of the OCT measuring light illuminating the object region or by providing a light source generating OCT measuring light having adjustable spectral width.

The reason for providing an adjustable spectral width of the OCT measuring light illuminating the object region in the case where principles of that Swept-Source OCT are employed, and the reason for providing an adjustable spectral width of the detected plural spectral portions of the superimposed light, in the case where principles of Spectral Domain-OCT are employed, is to enable adjusting an axial field of view of the OCT facility. The axial field of view represents a range of depth within the object, from which structure information can be obtained using the OCT facility. Changing the axial field of view may concurrently involve changing an axial resolution. Changing the axial field of view may have advantageous in certain applications, in particular of ophthalmologic applications where different portions of the eye are examined. For example, particular anatomical structures within the eye may have different extensions in an axial direction, i.e. a depth direction, thus requiring different axial field of views for imaging these anatomical structures.

Further, it may be advantageous to change a lateral resolution of structure data generated by the OCT facility when examining different objects. This is enabled in embodiments of the present invention by providing an adjustable lateral width of the beam of the OCT measuring light illuminating at least part of the object region. In particular, a lateral resolution may be defined as twice of the lateral width of the beam of the OCT measuring light. Changing the lateral width of the beam of the OCT measuring light may partly be achieved by varying the optical power of the illumination optics.

According to an embodiment of the present invention the imaging system comprising an OCT facility further comprises an objective lens system having adjustable optical power for imaging the object region to an image region, thereby providing a microscopy facility, wherein the light source, the objective lens system and the illumination optics are configured such that the beam of the OCT measuring light traverses the illumination optics and the objective lens system. Thus, an imaging system is provided integrating a microscopy facility and an OCT facility, wherein the OCT facility allows to adjust an axial field of view and a lateral resolution, and wherein the OCT measuring light traverses the objective lens system used to image the object region to the image region for visual inspection by an observer.

According to an embodiment of the present invention a wavelength of the OCT measuring light is in a range between 700 nm and 1350 nm, in particular between 1000 nm and 1100 nm. OCT measuring light having these wavelengths may penetrate human tissue several millimeters. In particular, OCT measuring light having these wavelengths is suitable for examination of a human eye.

According to an embodiment of the present invention the illumination optics comprises a first lens having a first focal length and a second lens having a second focal lengths different from the first focal length, which are alternatively arrangeable in a beam path of the OCT measuring light, wherein a distance between an exit area of the light source and the first lens amounts to the first focal length, when the first lens is arranged in the beam path of the OCT measuring light, and wherein a distance between the exit area of the light source and the second lens amounts to the second focal length, when the second lens is arranged in the beam path of the OCT measuring light. In the case, where principles of Spectral-Domain OCT are employed, the light source may comprise a Super-Luminescence-Diode (SLD) and in the case, where principles of Swept-Source OCT are employed the light source may comprise an optical amplifier, such as a semi-conductor optical amplifier (SOA), an optical fiber, such as a ring fiber, and at least one spectral filter, such as a Fabry-Pérot type spectral filter, that is arrangeable downstream the optical amplifier. Further, the light source may comprise an optical fiber for supplying the OCT measuring light to the illumination optics. In this case the exit area of the light source may be considered as a tip of the optical fiber emitting the OCT measuring light for traversing the illumination optics. The OCT measuring light emitted from the tip of the optical fiber may be described as a beam of OCT measuring light having a beam width and a beam divergence. In the case of a Gaussian beam the beam width is also known as the beam waist. In this case the beam waist is related to the beam divergence being a spreading angle of the beam. The beam width may be related to a diameter of the tip of the optical fiber. When arranged in the beam path of the OCT measuring light the exit area of the light source, in particular the tip of the optical fiber, is located in a focal plane of the first lens, i.e. offset by the first focal length from a principal plane of the first lens. Thus, after having traversed the first lens the OCT measuring light substantially constitutes a parallel beam bundle having a first cross-sectional area. When alternatively the second lens is arranged in the beam path of the OCT measuring light, the tip of the optical fiber is arranged in a focal plane of the second lens, such that the OCT measuring light having traversed the second lens is substantially constituted by a parallel beam bundle having a second cross-sectional area different from the first cross-sectional area. Thereby, a lateral width of the beam of the OCT measuring light illuminating the object region is adjustable.

Instead of or in addition to using lenses for adjusting the lateral with of the beam of the OCT measuring light also other optical elements, such as reflective or/and diffractive optical elements, such as mirrors or diffraction gratings, may be employed.

According to an embodiment of the present invention the imaging system further comprises an OCT scanner having at least one reflecting surface pivotable in at least one direction for scanning the OCT measuring light beam across the object region. The OCT scanner may be adapted to scan the OCT measuring light beam laterally across the object region, i.e. transverse to a direction of the OCT measuring light beam impinging onto the object. The OCT scanner may comprise two mirrors pivotable in two different directions.

The OCT scanner may comprise a first mirror pivotable around a first axis, a second mirror pivotable around a second axis, and an imaging optics to image a point at the first mirror on the first axis to a point at the second mirror on the second axis.

When scanning the OCT measuring light beam across the object region the OCT measuring beam may be incident on the object region at different position as measuring light spots having a diameter equal to the width of the beam of OCT measuring light at the object region. The entirety of areas of the spots may cover an entire area of the object region. Alternatively, the spots may be separated leaving areas of the object region not illuminated by the OCT measuring light. In this case a distance between a center of one spot and a center of a closest other spot may be greater than the width of the beam of OCT measuring light.

According to an embodiment of the present invention the imaging system is configured to adapt a first operation mode, wherein the object region is a first object region, and to adapt a second operation mode, wherein the object region is a second object region arranged farther away, in particular at least 20 mm, from the objective lens system than the first object region along a beam path of the OCT measuring light illuminating the object region. Thereby, the imaging system according to this embodiment is suitable to examine an anterior portion of a human eye as well as a posterior portion of the human eye.

According to an embodiment of the present invention the imaging system further comprises an ophthalmic lens arrangeable in the beam path of the OCT measuring light between the object region and the objective lens system, wherein the ophthalmic lens is arranged in the beam path of the OCT measuring light between the object region and the objective lens system in the second operation mode, and the ophthalmic lens is arranged outside the beam path of the OCT measuring light in the first operation mode. Thereby, it is possible to examine in the first operation mode the anterior portion of the human eye, i.e. for example the cornea, the anterior chamber, the posterior chamber and surrounding tissue, and to examine in the second operation mode the posterior portion of the eye, i.e. for example in particular the retina and parts of the optic nerve.

According to an embodiment of the present invention the lateral width of the beam of OCT measuring light illumination the object region is a first lateral width in the first operation mode and the lateral width of the beam of OCT measuring light illuminating the object region is a second lateral width in the second operation mode, which is smaller, in particular at least two times, than the first lateral width. Thus, the lateral resolution in the second operation mode is smaller, in particular at least two times, than the lateral resolution in the first operation mode.

According to an embodiment of the present invention in the first operation mode the spectral width of the OCT measuring light illuminating the object region is a first spectral width of the OCT measuring light illuminating the first object region, and in the second operation mode the spectral width of the OCT measuring light illuminating the object region is a second spectral width of the OCT measuring light illuminating the second object region, and wherein in the first operation mode the spectral width of the detected plural spectral portions is a first spectral width of the detected plural spectral portions, and in the second operation mode the spectral width of the detected plural spectral portions is a second spectral width of the detected plural spectral portions, wherein at least one of the following holds: the first spectral width of the OCT measuring light illuminating the first object region is smaller, in particular at least two times, than the second spectral width of the OCT measuring light illuminating the second object region; the first spectral width of the detected plural spectral portions is smaller, in particular at least two times, than the second spectral width of the detected plural spectral portions. The smaller spectral width in the first operation mode enables the spectral information to be sampled more finely. The finer information in the spectrum results in a greater axial field of view in the first operation mode than in the second operation mode. Thereby, an axial field of view in the first operation mode can be adjusted to be different from an axial field of view in the second operation mode. In particular for examining a human eye the axial field of view when imaging the anterior portion of the eye may be larger than the axial field of view when imaging the posterior portion of the eye in the second operation mode. This is in particular applicable for different types of Frequency-Domain OCT facilities.

According to an embodiment of the present invention a spectral width of the light source is adjustable, wherein in the first operation mode the spectral width of the light source is adjusted to the first spectral width of the OCT measuring light illuminating the first object region, and in the second operation mode the spectral width of the light source is adjusted to the second spectral width of the OCT measuring light illuminating the second object region. This embodiment is in particular applicable, when principles of Swept-Source OCT are employed. As mentioned above, the light source in this case may comprise a pumped optical amplifier that is optically connected to a ring fiber. The optical amplifier may have the capability to amplify light within a particular working range of wavelengths. In the beam path of the amplified light at least one spectral filter may be arranged whose transmission characteristics substantially defines a spectrum of light traversing the optical ring fiber and finally exiting therefrom for illuminating the object region. In particular, Fabry-Pérot type spectral filters may be employed comprising reflecting surfaces whose relative distance may effect a peak wavelength of the amplified light exiting the optical ring fiber. A characteristics of reflectivities of the opposing reflecting surfaces may effect a spectral width of the light exiting the optical ring fiber. Thus, providing spectral filters having different characteristics of their reflecting surfaces enables providing OCT measuring light illuminating the object region having different spectral widths.

According to an embodiment of the present invention a peak wavelength of the OCT measuring light in the first operation mode and in the second operation mode is sweepable. Thus, the object region is illuminated with OCT measuring light having a substantially constant spectral width, but having peak wavelengths varying over time.

According to an embodiment of the present invention the imaging system further comprises at least one spectral filter arrangeable in the beam path of the OCT measuring light illuminating the object region, wherein the spectral filter is arranged in the beam path of the OCT measuring light in one of the first operation mode and the second operation mode and wherein the spectral filter is arranged outside the beam path of the OCT measuring light in the other of the first operation mode and the second operation mode.

In particular, when principles of Spectral-Domain OCT are employed, an embodiment according to the present invention further provides a spectrometer having an adjustable dispersion strength for spectrally dispersing the OCT measuring light returned from the object region and superimposed with reference light to provide the plural spectral portions, wherein in the first operation mode the dispersion strength is greater, in particular at least two times, than in the second operation mode. A spectrometer spatially separates different spectral portions of the superimposed light. The greater the spatial separation of the spectral portion the greater the dispersion strength. The spectrometer may comprise refractive and/or diffractive and/or reflective optical elements. These may comprise for example a diffraction grating, a lens, a prism, and the like. Different dispersion strengths may be realized by providing for example two diffraction gratings having different lattice constants which are alternatively arrangeable for dispersing the superimposed light. Alternatively, an optical system having variable optical power may be arranged downstream of a diffraction grating to alter the special separation of the plural spectral portions dispersed by the diffraction grating. This may involve displacing a positionally resolving detector in dependence of the adjusted optical power of the optical system.

According to an embodiment of the present invention the spectrometer comprises a lens system having variable optical power arranged upstream of the detector.

According to an embodiment of the present invention the detector is a spatially resolving detector. The detector may comprise several detector segments, such as pixels, which individually detect intensities of light impinged thereon. A spectral width of light received by a single detector element is related to the axial field of view of the structure data acquired by the OCT facility.

The foregoing as well as other advantageous features of the invention will be more apparent from the following detailed description of preferred embodiments of the invention with reference to the accompanying drawings.

DETAILED DESCRIPTION OF THE INVENTION

Figure 1A:
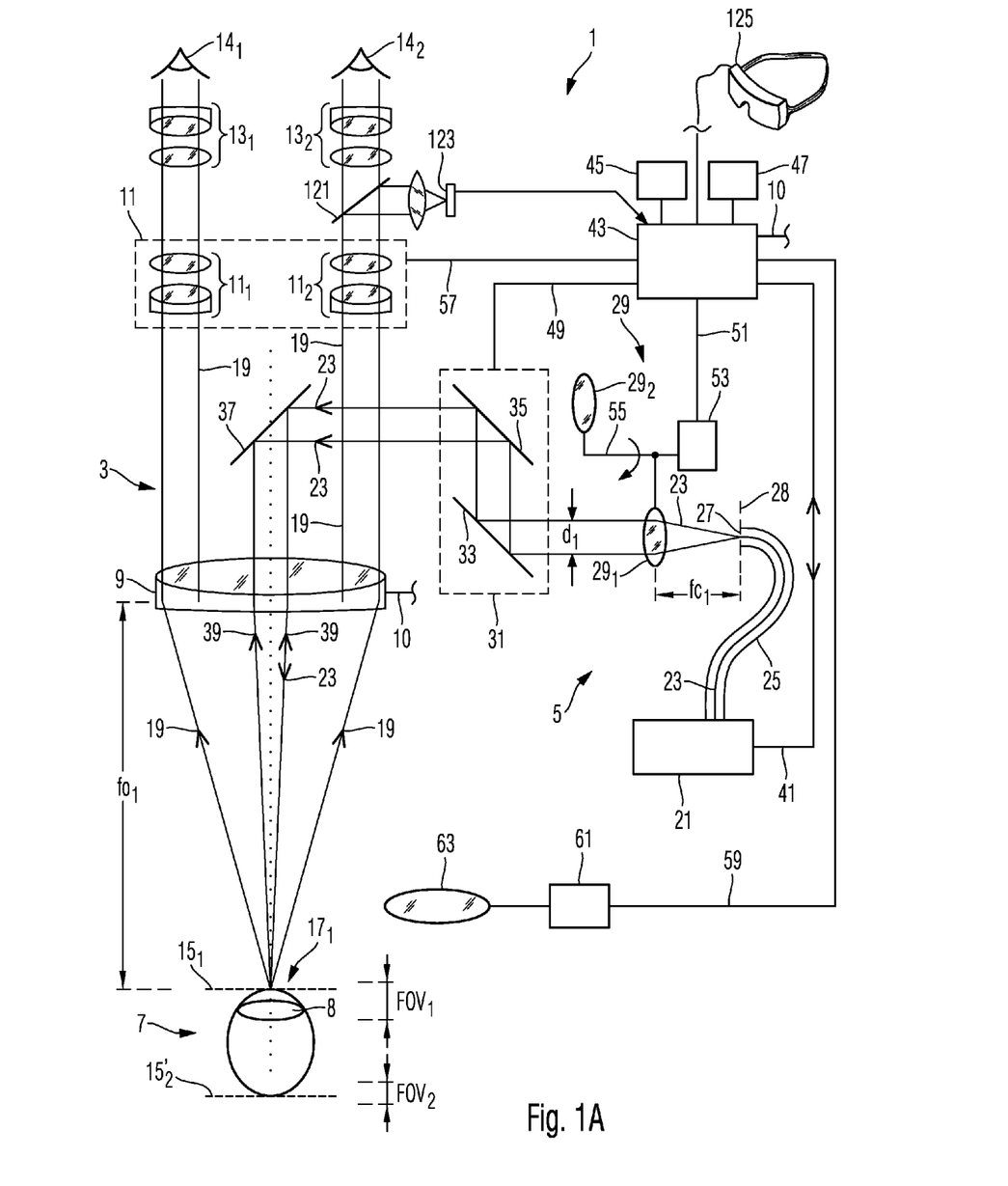
FIG. 1A schematically illustrates an imaging system according to an embodiment of the present invention in a first operation mode.

FIG. 1A schematically illustrates an imaging system 1 according to an exemplary embodiment of the present invention in a first operation mode. Imaging system 1 provides a microscope feature embodies as a microscope portion 3 as well as an OCT feature embodied as an OCT portion 5. In the illustrates example, a human eye 7 is investigated using the imaging system 1. The microscope portion 3 allows visual inspection of the eye 7, in particular visual stereoscopic inspection of the eye 7. In particular, microscopic images of the eye 7 may be acquired. For this purpose, the eye 7 is illuminated by a microscopy illumination light source (not shown in FIG. 1A) generating microscopy illumination light having wavelengths in the visible wavelength range. Depending on the application, an angle of incidence of the microscopy illumination light and a colour temperature of microscopy illumination light may be varied. In spite of these possible adaptations regarding the microscopy illumination light, it is not easy to inspect the eye 7 by visual inspection only, since the eye comprises a number of transparent anatomical structures that can hardly be resolved or recognized. Therefore, for a thorough investigation of the eye 7 the imaging system 1 provides an OCT feature by the OCT portion 5. The OCT feature allows to acquire structural volume data of the eye 7. Thus, the OCT facility allows acquiring data across a lateral extension and a depth (or axial) extension of the eye 7.

Figure 1B:
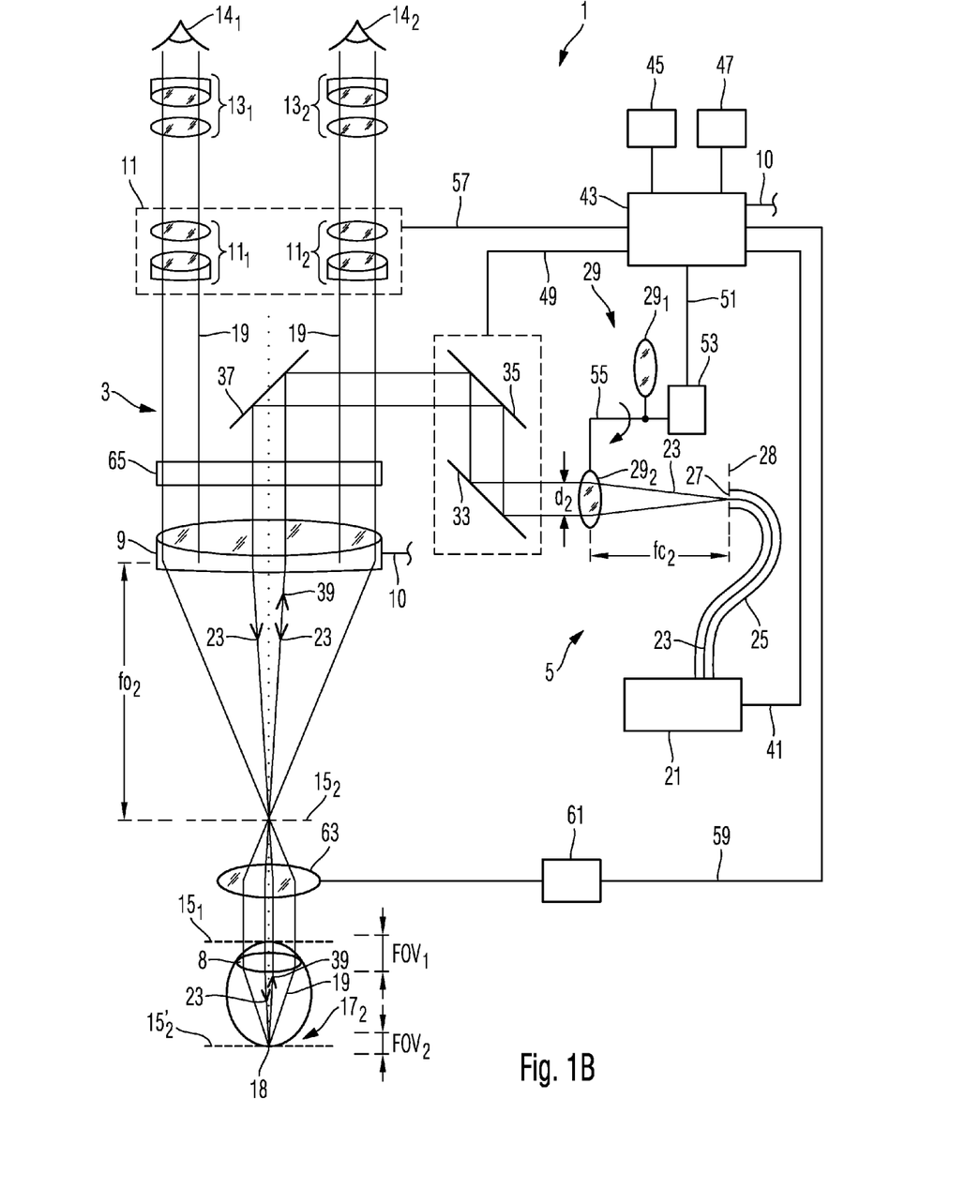
FIG. 1B schematically illustrates the imaging system according to FIG. 1A in a second operation mode.

The imaging system 1 according to the illustrated example allows to inspect the eye 7 by visual microscopy and optical coherence tomography both in the anterior portion of the eye 7 and in the posterior portion of the eye 7. For this, the imaging system 1 is configured to provide a first operation mode for inspecting the anterior portion, as illustrated in FIG. 1A, and a second operation mode for inspecting the posterior, as illustrated in FIG. 1B.

The imaging system 1, comprises an objective lens system 9 having adjustable optical power that is located in a beam path of both the microscope portion 3 and the OCT portion 5. The microscope portion 3 comprises a stereoscopic optical system downstream the objective lens system. This stereoscopic optical system comprises a zoom system 11 comprising a zoom lens $11_1$ and zoom lens $11_2$ and an ocular system 13 comprising an ocular lens $13_1$ which is viewed by a left eye $14_1$, and an ocular lens $13_2$. which is viewed by a right eye $14_1$ of an observer. In the first operation mode illustrated in FIG. 1A the objective lens system is adjusted to have a focal length $fo_1$. In a focal plane $15_1$ of the objective lens system 9 adjusted to have a focal length $fo_1$ the object region $17_1$ is arranged. The object region $17_1$ includes the anterior portion of the eye 7. The anterior portion of the eye comprises for example the cornea, the anterior chamber, the posterior chamber and a crystal lens 8 of the eye 7. Microscopy illumination light is scattered and reflected from the object region $17_1$ and emerges therefrom as light 19. The light 19 traverses the objective lens system 9. One part of light 19 traverses the zoom lens $11_1$ and thereafter the ocular lens system $13_1$, to enter e.g. the left eye $14_1$ of the observer. Another part of the light 19 having traversed the objective lens system 9 traverses the zoom lens $11_2$ and the ocular system $13_2$ to enter the right eye $14_2$ of the observer, such that the observer perceives a stereoscopic image of the object region $17_1$. The microscope portion may comprise a beam splitter 121 arranged downstream of the objective lens in the beam path of one or both parts of the light 19 to direct these parts of light 19 a image sensors 123, such as a CCD detectors, in order to record and store electronic representations of images of the object region $17_1$. These recorded images can be displayed via displays, such as a monitor, in particular a stereo display, or a head mounted display 125 carried by the observer.

The OCT portion 5 includes a spectrometer 21 which includes a light source, a beam splitter, a reference arm and a detector. The measuring arm of the interferometer carries OCT measuring light 23 that is supplied to an optical fiber 25. The optical fiber 25 guides the OCT measuring light 23 to a tip 27 of the optical fiber 25 which represents an exit area of the light source comprised in OCT spectrometer 21. The exit area at the tip 27 of the optical fiber 25 may correspond to a tip end of the core of the optical fiber 25 which guides the OCT measuring light 23. The OCT measuring light 23 emanates from the exit area at the tip 27 of the optical fiber as a divergent beam.

The exit area at the tip 27 of the optical fiber from which the OCT measuring light 23 emanates is arranged in a focal plane 28 of a collimating lens $29_1$. The focal length of the collimating lens $29_1$ amounts to $fc_1$. The OCT measuring light 23 traverses the collimating lens $29_1$ and is collimated to form a substantially parallel beam bundle having a cross sectional diameter $d_1$. Thereafter, the collimated OCT measuring light enters a scanning system 31 including a first scanning mirror 33 pivotable about a first axis and a second scanning mirror 35 pivotable about a second axis extending in a direction different from a direction of extension of the axis of the first mirror. The scanning system 31 is provided to enable scanning of the OCT measuring light across the object region $17_1$.

After being reflected at the scanning mirrors 33 and 35 the OCT measuring light is reflected at a mirror 37 to direct the OCT measuring light 23 towards the objective lens system 9. In the illustrated example, the mirror 37 is arranged between the two stereoscopic beam paths traversed by the microscopy light 19. According to other examples, the mirror 37 is a semi-transparent mirror traversed by the microscopy light 19.

After being reflected from the mirror 37, the OCT measuring light 23 traverses the objective lens system 9 to be focused at the focal plane $15_1$ of the objective lens system 9 being adjusted to have the focal length $fo_1$. Thus, the exit area at the tip 27 of the optical fiber 25 is imaged by the collimating lens $29_1$ and the objective lens system 9 onto a part of the image region $17_1$. A size of the image of the exit area at the tip 27 of the optical fiber 25 determines a lateral width of the beam of the OCT measuring light 23 illuminating at least part of the object region $17_1$. The lateral width of the beam of the OCT measuring light 23 illuminating part of the object region $17_1$ limits a lateral resolution of the OCT portion.

The objective lens system 9 and the collimating lens $29_1$ form the illumination optics of the OCT portion 5 in the first operation mode. A magnification of this illumination optics, i.e. a ratio of a size of an image of an object and a size of the object, is given as a ratio between the focal length of the objective lens system 9, i.e. $fo_1$, and the focal length of the collimating lens $29_1$, i.e. $fc_1$. Thus, the magnification is $fo_1/fc_1$. Therefore may vary The magnification of the illumination optics can be varied by varying the focal length $fo_1$, the focal length $fc_1$ or both focal lengths $fo_1$ and $fc_1$. Such variation results in a variation of the lateral width of the OCT measuring light illuminating the object region $17_1$. It follows that the lateral resolution of the OCT portion of the imaging system can be varied by such variation of the one or both of the focal lengths $fo_1$ and $fc_1$.

The OCT measuring light 23 penetrates the object region $17_1$, i.e. the anterior portion of the eye 7, in a depth direction, i.e. a direction substantially orthogonal to the focal plane $15_1$. The OCT measuring light 23 interacts with tissue material within a volume portion defined by the lateral width of the OCT measuring light. Portions of the OCT measuring light are reflected at different positions with different strength depending on optical properties of tissue material located in this volume portion. Having interacted with the object region $17_1$ the OCT measuring light emerges as light 39 from the eye 7. The light 39 traverses the objective lens system 9, is reflected from the mirror 37, is reflected from the scanning mirrors 35 and 33, traverses the collimating lens $29_1$, enters the tip 27 of the optical fiber 25 and is guided to a beam splitter of the interferometer 21. At the beam splitter, the light 39 is superimposed with reference light having traversed the reference arm of the interferometer 21. The superimposed light generates an interference on a detector of the OCT portion.

According to time-domain OCT, a length of the reference arm of the interferometer is varied, and the detected light intensities are recorded in dependence of the length of the reference arm. The intensities recorded in dependence of the length of the reference arm are analyzed to obtain volume data representing the tissues of the anterior portion of the eye 7.

According to spectral-domain OCT, the superimposed light is guided to a spectrometer which disperses the superimposed light based on its wavelength and detects intensities of plural spectral portions of the superimposed light. Thereby, a spectrum of the superimposed light is obtained. Electrical signals corresponding to the spectrum are then supplied via signal line 41 to a control and processing system 43. The control and processing system 43 processes the electrical signals, such as performing a Fourier transformation, sampling, normalization and the like to compute volume data representing tissues of the eye 7 within the object region $17_1$.

Moreover, other embodiments can use other OCT methods, such as swept source OCT for obtaining the volume data representing tissues of the eye 7 within the object region $17_1$.

In order to allow communication with a user, an input unit 45, such as a keyboard and a mouse, and a display unit 47 for visualizing the volume data, such as a monitor, can be connected to the control and processing system 43. Via a signal line 49 the control and processing system 43 is also connected to the scanning unit 31, to control rotational movements of the mirrors 35 and 33, in order to scan the beam of OCT measuring light 23 across the object region $17_1$.

Further, the control and processing unit 43 controls via the signal line 41 the spectrometer comprised in the interferometer 21 in order to adjust a dispersion strength of the spectrometer. The dispersion strength of the spectrometer is related to the spectral resolution of the detected spectrum of the dispersed superimposed light, and thus to the spectral width of the detected plural spectral portions of the dispersed superimposed light. This spectral resolution is related to an axial field of view (FOV) of the obtained OCT data. The spectral width is also related to an axial field of view of the OCT data. The field of view corresponds to a depth range within the object region from which structure information can be obtained by the OCT portion. In the first operation mode the dispersion strength of the spectrometer is adapted by the control and processing system 43 such that the field of view is $FOV_1$, as indicated in FIG. 1A.

In a time-domain OCT system, the field of view is $FOV_1$ is adjusted by controlling a scanning movement of a mirror in the reference arm of the interferometer.

Further, via signal line 51 the control and processing unit 43 controls an actuator 53 being adapted to rotate a carrier or shaft 55 on which the collimating lens $29_1$ and a further collimating lens $29_2$ are attached. In other embodiments, the collimating lenses $29_1$ $29_2$ are attached to a slider moved by the actuator to be translated in a linear direction.

The actuator 53 is controlled by the control and processing unit 43 to arrange either the collimating lens $29_1$ or the collimating lens $29_2$ into a beam path of the OCT measuring light 23 downstream the exit area at the fiber tip 27 of the optical fiber 25. The collimating lenses $29_1$ and $29_2$ have different focal lengths, the collimating lens $29_1$ has focal length $fc_1$ and the collimating lens $29_2$ has focal length $fc_2$ that is greater than the focal length $fc_1$. As explained above, changing the focal length of the collimating lens changes the lateral width of the OCT measuring light 23 illuminating the object region $17_1$ or object region $17_2$ as explained below.

Thus, the control and processing unit 43 is capable of controlling the lateral width of the OCT measuring light illuminating the object region, and thus of adjusting the lateral resolution of structural data acquired by the OCT portion 5.

According to a particular example in the first operation mode, the exit area at the tip 27 of the optical fiber 25 may have a diameter of around 5 μm, and a lateral width of the OCT measuring light 23 at the object region may be around 60 μm, thus requiring a magnification of the illumination optics comprising the collimating lens $29_1$ and the objective lens system 9 of around 10. This magnification may for example be achieved, if the focal length $fo_1$ of the objective lens system 9 is around 200 mm and the focal length $fc_1$ of the collimating lens $29_1$ is around 20 mm. The dispersion strength of the spectrometer of the OCT facility may be adjusted such that the field of view in the first operation mode, i.e. $FOV_1$, is around 3 to 7 mm.

Further, via signal line 57 the control and processing system 43 can control by appropriate actuators a magnification of the zoom system 11. The magnification of the zoom system 11 may in particular be controlled depending on a size of a scanning area of the OCT measuring light 23 which is defined by maximum rotations of the scanning mirrors 33 and 35. In particular, the control and processing system 43 may be adapted to substantially match a size of a microscopic field of view determined by a magnification of the zoom system 11 and the size of the scan area of the OCT measuring light. For example, if a user manually changes the magnification of the zoom system 11, the control and processing system 43 can automatically control the scanning unit 31 to match the scan area of the OCT measuring light with the microscopic field of view.

FIG. 1B schematically illustrates the imaging system 1 illustrated in FIG. 1A in the second operation mode. In the second operation mode an object region $17_2$, i.e. the posterior portion of the eye 7, is investigated. For this purpose, several components of the imaging system 1 have been readjusted compared to their condition during the first operation mode illustrated in FIG. 1A: An actuator 61, which can be manually controlled or controlled via signal line 59 by the control and processing system 43, mounts an ophthalmic lens 63 between the objective lens system 9 and the eye 7. Optionally, the focal length of the objective lens system 9 has been manually adjusted or adjusted via signal line 10 by the control and processing system 43 to be $fo_2$. Further, an inversion system 65 has been introduced into the beam path of the light 19 to compensate up-down and right-left inversion caused by introducing the ophthalmic lens 63 such that the image perceived by the user looking into the oculars 13 is an upright image.

Further, the collimating lens $29_1$ has now been replaced by collimating lens $29_2$ to be arranged in the beam path of the OCT measuring light 23 downstream the exit area at the tip 27 of the optical fiber 25. Collimating lens $29_2$ has a focal length $fc_2$ and the exit area at the tip 27 is arranged in the focal plane 28 of the collimating lens $29_2$. The focal length $fc_2$ is greater than the focal length $fc_1$. In the illustrated example, the focal length $fc_2$ is two times the focal length $fc_1$. In particular, the focal length $fc_2$ may be about 30 mm to 50 mm. The effect of the change from the collimating lens $29_1$ in the first operation mode to the collimating lens $29_2$ in the second operation mode is that the lateral width of the OCT measuring light illuminating now the object region $17_2$ is decreased, for example by a factor of more than 2.

The OCT measuring light 23 emanating as a divergent beam from the tip of the optical fiber 25, traverses the collimating lens $29_2$, is reflected from the scan mirrors 33 and 35 as substantially parallel beam bundle, is reflected by the mirror 37, traverses the objective lens system 9 to be focused at the focal plane $15_2$ which is arranged a distance $fo_2$ away from the objective lens system 9. At the focal plane $15_2$ the convergent OCT measuring light 23 crosses, and traverses the ophthalmic lens 63, to form a substantially parallel beam bundle. This substantially parallel beam bundle of OCT measuring light 23 traverses the crystal lens 8 of the eye to be focused on the retina 18 of the eye in the object region $17_2$. The OCT measuring light 23 interacts with the object region $17_2$ in a depth range corresponding to the axial field of view $FOV_2$ and leaves the object region $17_2$ as light 39. Light 39 traverses the crystal lens 8, the ophthalmic lens 63, the objective lens system 9, the inversion system 65, is reflected at the folding mirror 37, the two scanning mirrors 35 and 33, traverses the collimating lens $29_2$ and is supplied to the optical fiber 25 which guides the light 39 to the interferometer 21 of the OCT facility 5, as described above.

In the second operation mode the dispersion strength of the spectrometer (within interferometer 21) for wavelength dispersion of the light 39 superimposed with reference light has been set to be smaller than in the first operation mode. Thus, the axial field of view in the second operation mode, i.e. $FOV_2$, is smaller, in particular more than two times smaller, than the field of view in the first operation mode, i.e. $FOV_1$. Thus, for switching from the first operation mode to the second operation mode the control and processing system 43 has at least controlled the actuator 53 to cause switching from the collimating lens $29_1$ to the collimating lens $29_2$. The control and processing system 43 may also control the spectrometer to change the dispersion strength. The control and processing system 43 may also control the objective lens system 9 to change the focal length from $fo_1$ to $fo_2$. The control and processing system 43 may also control the actuator 61 to place the ophthalmic lens 63 in a beam path of the OCT measuring light and the microscopic light thereby changing from the object region $17_1$ to the object region $17_2$ which is located farther away from the objective lens system 9 than the object region $17_1$.

Figure 2:
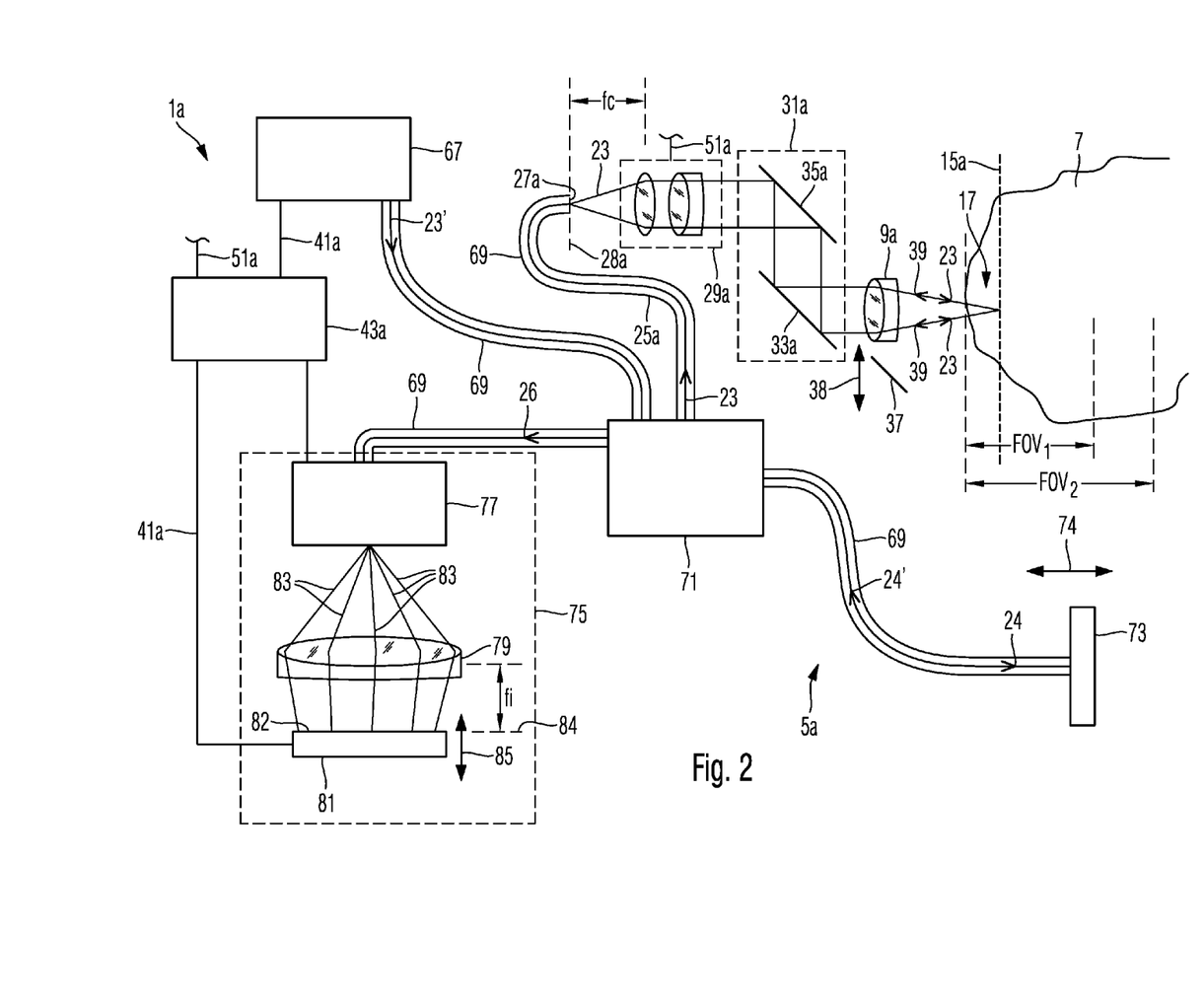
FIG. 2 schematically illustrates an imaging system, in particular a Spectral-Domain OCT facility according to an embodiment of the present invention.

FIG. 2 schematically illustrates another embodiment 1$a$ of an imaging system. As will be explained below, the imaging system 1$a$ may also be used to provide the OCT portion 5 of the embodiment illustrated with reference to FIGS. 1A and 1B above. The imaging system 1$a$ provides an OCT feature embodied as a Spectral Domain OCT. The OCT portion 5$a$ comprises a light source 67 for generating a beam of OCT measuring light 23' which is guided by an optical fiber 69 to a beam splitter/coupler 71. The beam splitter/coupler 71 splits the OCT measuring light 23' into a portion 23 and a portion 24. Portion 24 of the OCT measuring light is guided via an optical fiber 69 to a reference mirror 73 which can be displaced in directions indicated by double arrow 74. Portion 24 of the OCT measuring light is reflected from the reference mirror 73 and is guided as light 24' to the optical splitter/coupler 71. Portion 23 of the OCT measuring light is guided by optical fiber 25$a$ to a tip 27$a$ of the optical fiber 25$a$ from which the portion 23 of the OCT measuring light emanates as a divergent beam and traverses a collimating optics 29$a$ having adjustable optical power. The collimating optics 29$a$ may be constructed as a zoom system such that a focal length thereof can be changed continuously or in one or more steps. The OCT measuring light 23 is collimated by collimating optics 29$a$, is reflected from mirrors 33$a$ and 35$a$ of a scanning system 31$a$, traverses a lens system 9$a$ to be focused in a focal plane 15$a$ of the lens system 9$a$ in object region 17. Light 39 emanating from the object region traverses lens system 9$a$, is reflected from the scanning mirrors 35$a$ and 33$a$, traverses the collimating optics 29$a$, enters the optical fiber 25$a$ and is guided to the beam splitter/coupler 71, where it is superimposed with the light portion 24', to form superimposed light 26. Superimposed light 26 is guided via optical fiber 69 to a spectrometer 75.

Spectrometer 75 includes a dispersion apparatus 77, imaging optics 79 and a spatially resolving detector 81. The dispersion apparatus 77 may comprise diffractive and/or refractive optical elements for dispersing the superimposed light 26. Dispersing the superimposed light 26 typically comprises deflecting spectral portions of the superimposed light 26 in different directions depending on wavelengths comprised in the spectral portions. The dispersion apparatus 77 may for example comprise a diffraction grating including a substrate having plural diffractive elements arranged thereon, in particular arranged in a periodic manner. The dispersion apparatus 77 disperses the superimposed light 26 into plural spectral portions 83. The plural spectral portions 83 traverse the imaging optics 79 having adjustable optical power. The detector 81 is arranged in the focal plane 84 of the imaging optics 79. Thus, a distance between an effective surface 82 of the detector 81 and a principal plane of the imaging optics 79 corresponds to the focal length fi of the imaging optics 79. When the focal length fi of the imaging optics 79 is changed, the detector 81 is shifted in directions indicated as double arrow 85 to keep the effective surface 82 of the detector 81 arranged in the changed focal plane 84 of the imaging optics 79. The detector 81 comprises plural detector segments each receiving a particular spectral portion 83 of the dispersed superimposed light 26. By changing the focal length fi of the imaging optics 79 and displacing the detector 81 as explained above, a width of a wavelength range comprised in a spectral portion received and detected by a single detector segment can be controlled. This width of a wavelength range detected by a single detector segment is related to the axial field of view provided by the OCT facility 5a. Thereby, the OCT facility 5a is enabled to adjust an axial field of view to for example a value of $FOV_1$ or a value of $FOV_2$, as indicated in FIG. 2.

Further, by varying the focal length fc of the collimating optics 29a and arranging the fiber tip 27a in the focal plane 28a of the collimating optics 29a the lateral width of the beam of OCT measuring light 23 illuminating the object region 17 can be controlled. Thus, the OCT facility 5a is also capable of adjusting a lateral resolution.

As explained above, the imaging system 1a providing an OCT feature may be employed as the OCT portion 5 in the imaging system 1 illustrated with reference to FIGS. 1A and 1B above. For this purpose, the OCT measuring light 23 may be guided through the objective lens system 9 instead of the lens system 9a by providing a mirror 37a instead of the lens system 9a as indicated by double arrow 38.

The imaging system 1a also comprises a control and processing system 43a performing similar functions as the control and processing system 43 of imaging system 1 illustrated in FIGS. 1A and 1B illustrated with reference to FIGS. 1A and 1B above. In particular, the control and processing system 43a obtains data from the detector 81 via signal line 41a and controls also displacing the detector 81 in directions indicated by double arrow 85. Further, system 43a controls adjusting of the focal length fi of the imaging optics 79 and thus controls adjusting the dispersion strength of the spectrometer 75. Further, via signal line 51a the control and processing system 43a controls adjusting the focal length fc of the collimating system 29a.

Figure 3:
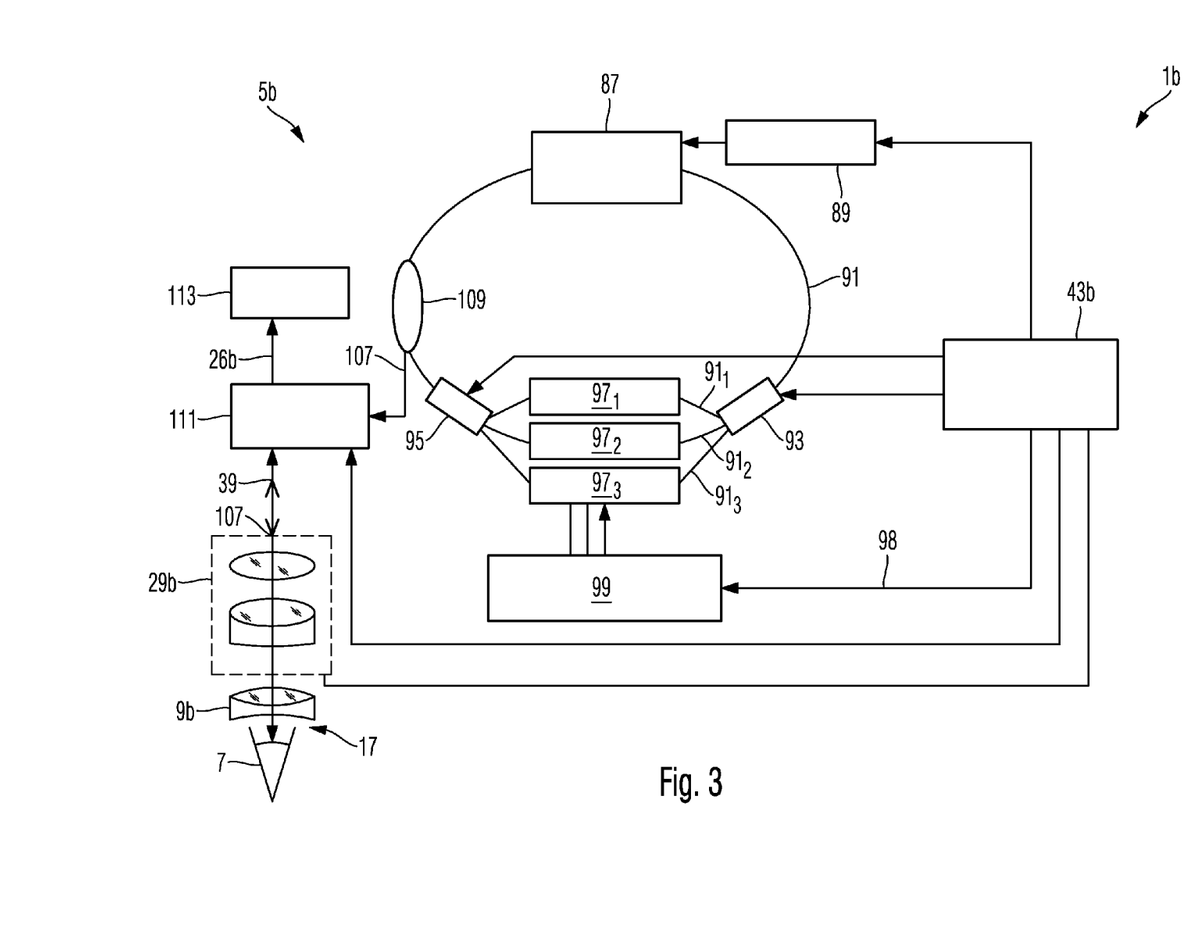
FIG. 3 schematically illustrates an imaging system, in particular a Swept-Source OCT facility, according to an embodiment of the present invention.

FIG. 3 illustrates another embodiment of an imaging system 1b according. In particular, FIG. 3 schematically illustrates an imaging system 1b providing an OCT feature embodied as a swept-source OCT. The swept-source OCT 5b illustrated in FIG. 3 can be used to form provide the OCT portion in the embodiment illustrated with reference to FIGS. 1A and 1B above. In particular, also the swept-source OCT 5b illustrated in FIG. 3 can be controlled to adjust an axial field of view of the OCT imaging as well as a lateral resolution of the OCT imaging.

The swept-source OCT 5b comprises an optical amplifier 87 for amplifying light waves in a predetermined wavelength range. For this purpose, the optical amplifier 87 can be a semi-conductor optical amplifier pumped by a current source 89. The optical amplifier 87 is optically connected to a ring fiber 91 for guiding light amplified by the optical amplifier 87. In a beam path provided by the optical fiber 91 routing switches 93 and 95 are configured to guide light propagating within the optical fiber 91 to optical fiber $91_1$, $91_2$, and $91_3$. Optical fiber $91_1$ guides light received from routing switch 93 or routing switch 95 to a first sweepable filter $97_1$. After traversing the first sweepable filter $97_1$ the filtered light is again coupled into the fiber ring 91 via routing switch 93 or 95.

Alternatively to traversing the first sweepable filter $97_1$ the routing switches 93 and 95 may cause the light in the ring 91 to be guided through a second sweepable filter $97_2$ or a third sweepable filter $97_3$. The first, second and third sweepable filters $97_1$, $97_2$, and $97_3$ may be spectral filters of the Fabry-Pérot type comprising two opposing reflecting surfaces arranged parallel to each other. A distance between the two reflecting surfaces is can be controlled by a piezo-electric element controlled by a ramp generator 99 connected to the three spectral filters. Only light having a wavelength satisfying a resonance condition depending on a distance between the two opposing reflecting surfaces of the spectral filter arranged in the beam path of the ring 91 will constructively interfere. Light having other wavelengths will substantially be attenuated. By changing the distance between the two opposing reflecting surfaces of the Fabry-Pérot type filter using the ramp generator 99, a peak wavelength of light satisfying the resonance condition can be varied. Depending on the optical properties of the opposing reflecting surfaces of the Fabry-Pérot type filter arranged in the beam path of the ring fiber 91 not only a single wavelength will satisfy the resonance condition but a range of wavelengths around the peak wavelengths. Thus, a particular Fabry-Pérot type spectral filter is characterized by a particular transmission spectrum whose characteristics depends on at least a reflectivity of the reflecting surfaces.

Figure 4:
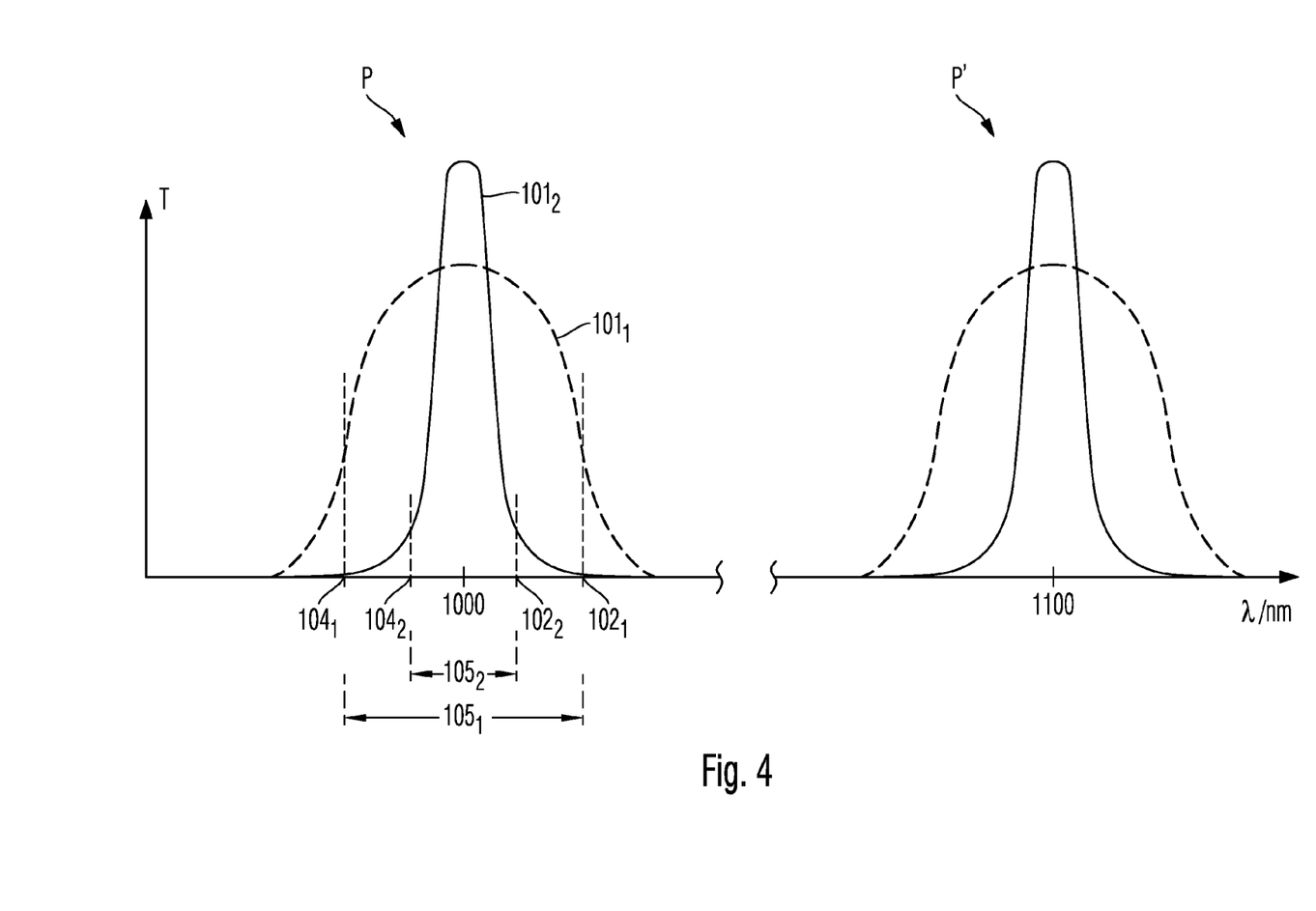
FIG. 4 illustrates a diagram of a spectrum of OCT measuring light that may be used in the Swept-Source OCT facility according to FIG. 3.

FIG. 4 is a diagram showing transmission characteristics T of the first and second sweepable filters $97_1$ and $97_2$. Depending on the wavelength λ, a transmission of the first sweepable filter $97_1$ is shown as a curve $101_1$, and a transmission of the second sweepable filter $97_2$ is shown as a curve $101_2$. Typically, each Fabry-Pérot type filter exhibits several transmission peaks. In FIG. 4 two such transmission peaks P, P' are shown, one having a mean wavelength of 1000 nm and another having a mean wavelength of 1100 nm. Plural transmission peaks occur, because the resonance condition may be satisfied by plural wavelengths according to different orders. Here, only the first transmission peak P located around 1000 nm is of interest, since the second transmission peak P' located around 1100 nm is located outside the working range of the semi-conductor optical amplifier 87 and is therefore not amplified.

As first spectral width $105_1$ of the transmission spectrum $101_1$ of the first sweepable filter $97_1$ may be obtained by forming a minimum of a difference between two wavelengths $102_1$ and $104_1$ within which 90% of the transmission $101_1$ of the first sweepable filter $97_1$ is comprised, whereby transmission peaks of higher order wavelengths outside the wavelength range of the semi-conductor optical amplifier 87 are disregarded. In the illustrated example, the first spectral width $105_1$ amounts to about 50 pm. Similarly, a second spectral width $105_2$ of the transmission spectrum $101_2$ of the second sweepable filter $97_2$ may be obtained amounting to about 20 pm.

Referring again to FIG. 3, when the first sweepable filter $97_1$ is arranged to be traversed by light guided within the ring fiber 91, only light will be amplified by the semi-conductor optical amplifier 87 that substantially has a spectrum given by the transmission spectrum $101_1$ of the first sweepable filter $97_1$, as illustrated in FIG. 4. Thus, a spectrum of light guided within the ring fiber 91 will be largely defined by the transmission characteristics of the spectral filter $97_1$ arranged within the ring fiber 91. Light thus amplified will be denoted as OCT measuring light 107. A portion of the OCT measuring light 107 is extracted by splitter 109 and is guided to interferometer 111. In the interferometer 111, the OCT measuring light is split into two portions, wherein one portion is reflected by a reference mirror and the other portion is directed to collimating optics 29b. The collimating optics 29b has an adjustable optical power similar to the collimating optics 29 illustrated in FIGS. 1A and 1B and collimating optics 29a illustrated in FIG. 2. Thus, these different embodiments of collimation optics provide a similar function in controlling a lateral width of OCT measuring light illuminating the object region 17 where the object 7 is arranged.

After having traversed the collimating optics 29b the OCT measuring light 107 traverses the lens system 9b to be focused at the object region 17. The OCT measuring light 107 illuminating the object region 17 interacts with the object 7, and light 39 emanates from the object, traverses the lens system 9b, collimating optics 29b and is guided to interferometer 111. Here, light 39 is superimposed with reference light to form superimposed light 26b. Superimposed light 26b is guided to photo detector 113 which detects an intensity of the superimposed light 26b.

Similar to the other embodiments of imaging systems illustrated above, the imaging system 1b comprises a control and processing system 43b that controls operation of the imaging system 1b. In particular, control and processing system 43b controls, via a signal line 98, the ramp generator 99 to enable sweeping of the peak wavelength of the OCT measuring light 107. Further, the system 43b may control adjusting the focal length of the collimating optics 29b and may also control the routing switches 93 and 95, thereby controlling a spectrum of the OCT measuring light 107 illuminating the object region 17. Thus, the control and processing system 43b may control and change an axial field of view and/or a lateral resolution of the OCT portion 5b.

When the lens system 9b is substituted with folding mirror 37 of the imaging system 1 illustrated in FIGS. 1A and 1B the OCT facility 5b may be used as OCT facility 5 in the imaging system 1 illustrated in FIGS. 1A and 1B.

Embodiments of the present invention provide imaging systems enabling examination of both the anterior portion of the eye and the posterior portion of the eye by visual microscopy and optical coherence tomography. In particular, these imaging systems allow switching of OCT components and microscopy components when examining the one or the other object region. In particular, an axial field of view and a lateral resolution of the OCT method are varied when switching the object regions.

While the present invention has been shown and described herein in what is believed to be the most practical and preferred embodiments, it is recognized that departures can be made therefrom within the scope of the invention, which is therefore not be limited to the details disclosed herein but is to be accorded the full scope of the claims so as to embrace any and all equivalent methods and apparatus.

What is claimed is:

1. An imaging system including a microscope system and an OCT system,
   wherein the microscope system is configured to image an object plane onto an image plane via an imaging beam path traversing an objective lens of the imaging system;
   wherein the OCT system comprises an OCT measuring beam emitter and OCT beam shaping optics, and is configured to provide an OCT beam path; and
   wherein the OCT system is further configured to direct OCT measuring light towards the object plane via the OCT beam path extending from the OCT measuring beam emitter and traversing the OCT beam shaping optics and the objective lens,
   wherein the OCT beam shaping optics is located outside of the imaging beam path and configured to change a lateral width of a beam waist of a beam of the OCT measuring light at the object plane, such that before and after the changing of the lateral width of the beam waist, the beam of the OCT measuring light is focused at the object plane.

2. The imaging system according to claim 1, further comprising at least one ocular located in the imaging beam path.

3. The imaging system according to claim 1, further comprising at least one image sensor located in the imaging beam path.

4. The imaging system according to claim 3, further comprising an image display configured to display light intensities detected by the at least one image sensor and representing an object located at the object plane.

5. The imaging system according to claim 4, wherein the image display comprises a head mounted display.

6. The imaging system according to claim 1, wherein the objective lens is characterized by a variable focal length.

7. The imaging system according to claim 1, wherein the OCT beam shaping optics are configured to change the lateral width of the beam waist from a maximum width to a minimum width, wherein the maximum width is at least two times greater than the minimum width.

8. The imaging system according to claim 1, wherein the OCT beam shaping optics is characterized by a variable focal length;
   wherein the changing of the lateral width comprises changing a value of the variable focal length.

9. The imaging system according to claim 1, wherein the OCT measuring beam emitter is located in a focal plane of the OCT beam shaping optics.

10. The imaging system according to claim 1, wherein the OCT beam shaping optics comprises
    at least two lenses,
    a carrier on which the at least two lenses are mounted and
    an actuator configured to move the carrier such that the two focusing lenses are alternately insertable into the OCT beam path;
    wherein the changing of the lateral width comprises the moving of the carrier.

11. The imaging system according to claim 8, wherein the imaging system is switchable to at least two operation modes with each operation mode having a different value of the variable focal length;
    wherein in each of the operation modes, the beam emitter is located in a focal plane of the beam shaping optics.

12. The imaging system according to claim 8, wherein the imaging system is switchable to at least two operation modes with each operation mode having a different value of the variable focal length;
    wherein in each of the operation modes, the beam shaping optics forms a substantially parallel beam bundle of the OCT measuring light.

13. The imaging system according to claim 12, wherein in each of the operation modes, a cross-sectional area of the substantially parallel beam bundle is different.

14. The imaging system according to claim 10, wherein the imaging system is switchable to at least a first and a second operation mode;
    wherein in the first operation mode, the first lens is inserted into the beam path of the OCT measuring light with the OCT beam emitter being arranged in a focal plane of the beam shaping optics; and
    wherein in the second operation mode, the second lens is inserted into the beam path of the OCT measuring light with the OCT beam emitter being arranged in a focal plane of the beam shaping optics.

15. The imaging system according to claim 10, wherein the imaging system is switchable to at least a first and a second operation mode;
    wherein in the first operation mode, the first lens is inserted into the beam path of the OCT measuring light and in the second operation mode, the second lens is inserted into the beam path of the OCT measuring light;
wherein in the first and the second operation modes, the beam shaping optics forms a substantially parallel beam bundle of the OCT measuring light.

16. The imaging system according to claim 15, wherein a cross sectional area of the substantially parallel beam bundle in the first operation mode is different from a cross-sectional area of the substantially parallel beam bundle in the second operation mode.

17. The imaging system of claim 1, wherein the imaging system is configured to switch from a first operation mode to a second operation mode;
wherein the switching from the first to the second operation mode comprises the changing of the lateral width.

18. The imaging system of claim 17, wherein the OCT beam shaping optics has a variable focal length;
wherein in the first operation mode, a value of the variable focal length is different from a value of the variable focal length in the second operation mode.

19. The imaging system of claim 18, wherein in the first operation mode, a cross-sectional area of a substantially parallel beam bundle of the OCT measuring light is different from the cross-sectional area in the second operation mode.

20. The imaging system of claim 17, wherein in the first operation mode, a cross-sectional area of a substantially parallel beam bundle of the OCT measuring light is different from the cross-sectional area in the second operation mode.

21. The imaging system of claim 17, wherein in the first and in the second operation modes, the beam shaping optics forms a substantially parallel beam bundle of the OCT measuring light.

22. The imaging system of claim 21, wherein in the first and the second operation modes, the beam emitter is located in a focal plane of the beam shaping optics.

23. The imaging system of claim 17, wherein in each of the first and the second operation modes, the beam emitter is located in a focal plane of the beam shaping optics.

24. The imaging system of claim 23, wherein in the first operation mode, a cross-sectional area of a substantially parallel beam bundle of the OCT measuring light is different from the cross-sectional area in the second operation mode.

25. The imaging system of claim 17, wherein the beam shaping optics comprises a first and a second lens which are alternately insertable into the OCT beam path;
wherein in the first operation mode, the first lens is inserted into the OCT beam path and in the second operation mode, the second lens is inserted into the OCT beam path.

26. The imaging system of claim 25, wherein in the first operation mode, a cross-sectional area of a substantially parallel beam bundle of the OCT measuring light is different from the cross-sectional area in the second operation mode.

27. The imaging system of claim 25, wherein in each of the first and in the second operation modes, the beam shaping optics forms a substantially parallel beam bundle of the OCT measuring light.

28. The imaging system of claim 25, wherein in each of the first and the second operation modes, the beam emitter is located in a focal plane of the beam shaping optics.

29. The imaging system of claim 17, wherein the imaging system comprises:
a controller configured to control the changing of the lateral width; and
an actuator which is connected to the beam shaping optics;
wherein the switching from the first operation mode to the second operation mode comprises controlling the actuator by the controller.

30. The imaging system of claim 29, wherein the OCT beam shaping optics has a variable focal length;
wherein in the first operation mode, a value of the variable focal length is different from a value of the variable focal length in the second operation mode.

31. The imaging system of claim 29, wherein in each of the first and in the second operation modes, the beam shaping optics forms a substantially parallel beam bundle of the OCT measuring light.

32. The imaging system of claim 29, wherein in the first operation mode, a cross-sectional area of a substantially parallel beam bundle of the OCT measuring light is different from the cross-sectional area in the second operation mode.

33. The imaging system of claim 29, wherein in each of the first and the second operation modes, the beam emitter is located in a focal plane of the beam shaping optics.

34. The imaging system of claim 29, wherein the beam shaping optics comprises a first and a second lens which are alternately insertable into the OCT beam path by the actuator;
wherein in the first operation mode, the first lens is inserted into the OCT beam path and in the second operation mode, the second lens is inserted into the OCT beam path.

35. The imaging system of claim 1, wherein before and after the changing of the lateral width, the beam shaping optics forms a substantially parallel beam bundle of the OCT measuring light.

36. The imaging system of claim 35, wherein a cross-sectional area of the substantially parallel beam bundle is different before and after the changing of the lateral width.

37. The imaging system of claim 35, wherein before and after the changing of the lateral width, the beam emitter is located in a focal plane of the beam shaping optics.

38. The imaging system of claim 35, wherein the beam shaping optics has a variable focal length;
wherein the changing of the lateral width comprises changing a value of the variable focal length.

39. The imaging system of claim 38, wherein before and after the changing of the lateral width, the beam emitter is located in a focal plane of the beam shaping optics.

40. The imaging system of claim 35, wherein the beam shaping optics comprises a first and a second lens;
wherein the changing of the lateral width comprises removing the first lens from the OCT beam path and inserting the second lens into the OCT beam path.

41. The imaging system of claim 40, wherein before and after the changing of the lateral width, the beam emitter is located in a focal plane of the beam shaping optics.

42. The imaging system of claim 1, wherein before and after the changing of the lateral width, the beam emitter is located in a focal plane of the beam shaping optics.

43. The imaging system of claim 42, wherein the changing of the lateral width comprises changing a cross-sectional area of a substantially parallel beam bundle of the OCT measuring light.

44. The imaging system of claim 42, wherein the beam shaping optics has a variable focal length;
wherein the changing of the lateral width comprises changing a value of the variable focal length.

45. The imaging system of claim 42, wherein the beam shaping optics comprises a first and a second lens;
wherein the changing of the lateral width comprises removing the first lens from the OCT beam path and inserting the second lens into the OCT beam path.

46. The imaging system of claim 1, wherein the changing of the lateral width comprises changing a cross-sectional area of a substantially parallel beam bundle of the OCT measuring light.

47. The imaging system of claim 46, wherein the beam shaping optics has a variable focal length;
   wherein the changing of the lateral width comprises changing a value of the variable focal length.

48. The imaging system of claim 46, wherein the beam shaping optics comprises a first and a second lens;
   wherein the changing of the lateral width comprises removing the first lens from the OCT beam path and inserting the second lens into the OCT beam path.

49. The imaging system of claim 48, wherein before and after the changing of the lateral width, the beam emitter is located in a focal plane of the beam shaping optics.

50. The imaging system of claim 1, wherein the beam shaping optics comprises a first and a second lens;
   wherein the changing of the lateral width comprises removing the first lens from the OCT beam path and inserting the second lens into the OCT beam path.

51. The imaging system of claim 50, wherein the beam shaping optics has a variable focal length;
   wherein the changing of the lateral width comprises changing a value of the variable focal length.

* * * * *